United States Patent [19]

Nunokawa

[11] Patent Number: 4,558,932
[45] Date of Patent: Dec. 17, 1985

[54] VARIABLE IMAGE MAGNIFICATION EYE FUNDUS CAMERA

[75] Inventor: Kazuo Nunokawa, Tokyo, Japan

[73] Assignee: Tokyo Kogaku Kikai Kabushiki Kaisha, Tokyo, Japan

[21] Appl. No.: 532,995

[22] Filed: Sep. 16, 1983

[30] Foreign Application Priority Data

Sep. 16, 1982 [JP] Japan ................................ 57-159427

[51] Int. Cl.⁴ ......................... A61B 3/14; B03B 29/00
[52] U.S. Cl. ....................................... 351/206; 354/62
[58] Field of Search ....................... 351/206, 207, 208; 354/62

[56] References Cited

U.S. PATENT DOCUMENTS 4,068,932 1/1978 Ohta .................................... 351/206
4,265,518 5/1981 Matsumura ......................... 351/206

FOREIGN PATENT DOCUMENTS 108623 8/1979 Japan .................................. 351/206

Primary Examiner—Rodney B. Bovernick
Attorney, Agent, or Firm—Fleit, Jacobson, Cohn & Price

[57] ABSTRACT

A variable image magnification eye fundus camera has an illuminating system in which there are provided an annular aperture (7a, 7b) in a position optically conjugate with the iris (R) of the eye (E) to be inspected, and means (7, 12) for adjusting in accordance with the angle of view the diameter of the image of the annular aperture formed by the illuminating system at the iris, whereby it is possible to make a clear photograph of the eye fundus even if the diameter of the pupil is relatively reduced.

7 Claims, 5 Drawing Figures

VARIABLE IMAGE MAGNIFICATION EYE FUNDUS CAMERA

FIELD OF THE INVENTION

The present invention relates in general to an eye fundus camera and, in particular, to an eye fundus camera in which the angle of view can be varied in accordance with the diameter of the pupil of the eye to be inspected.

BACKGROUND OF THE INVENTION

In a known eye fundus camera of this type, the illuminating system is provided with one or more annular apertures, through which light emitted from the light source is directed toward the eye fundus. The apertures are positioned such that their images are formed in the anterior part of the eye, and they limit the bundle of rays of light directed toward the fundus such that it does not overlap at the cornea or at the crystalline lens another bundle of rays of light which is reflected or scattered from the fundus and which is to be received by the photographing system. In this way, the known eye fundus camera is capable of escaping such detrimental reflection or scattering of light at the cornea or the crystalline lens as causes part of the light for illumination to travel back from the cornea or the crystalline lens into the photographing system.

In order to escape the detrimental reflection or scattering effectively, the diameters of the annular apertures must be made larger as the angle of view of the camera is made wider, or as the image magnification is made smaller. For this reason, in the case of a variable image-magnification eye fundus camera in which the angle of view is variable with the image magnification, the diameters of the annular images of the apertures in the anterior part of the eye, or the diameter of the annular cross section of the illuminating light ray bundle, must be large, as compared with those or that of an eye fundus camera with a fixed narrow angle of view, so as to escape the detrimental reflection or scattering of light to make a clear photograph of the eye fundus throughout the whole range of angle of view.

Thus, in the case of a person, such as an aged person or a diabetes mellitus patient, who cannot open the irises wide sufficiently, the eye fundus may be photographed with an eye fundus camera with a fixed narrow angle of view. A variable image-magnification eye fundus camera, however, cannot be used to make a photograph of such person's eye fundus, because the light directed to the eye is interrupted by the iris irrespectively of the angle of view.

It is thus an object of the present invention to provide an eye fundus camera of the type in which the angle of view is variable with the image-magnification, and in which the illuminating system is improved so that a sharp photograph can be taken at a narrow angle of view even if the pupil of the eye to be inspected is relatively reduced.

It is another object of the present invention to provide an eye fundus camera having an illuminating system which is improved so that the detrimental reflection or scattering of light as mentioned hereinabove can be avoided and thus a clear image of the eye fundus can be obtained throughout a wide range of angle of view.

SUMMARY OF THE INVENTION

In order to achieve these and other objects, the eye fundus camera according to the present invention comprises:

a first optical system for illuminating the fundus of the eye to be inspected, including at least one light source, and an annular aperture which is provided at a position optically conjugate with the iris of the eye and through which the light emitted from said light source is directed toward the eye so that an image of said annular aperture is formed at or near the iris;

a second optical system for making a photograph of the eye fundus illuminated by said first optical system, including a variable magnification lens system for varying the image magnification; and means for adjusting the size of said image of said annular aperture, including means for adjusting the inner diameter of said image.

Said illuminating system preferably further comprises another annular aperture provided in a position optically conjugate with the cornea of the eye.

BRIEF DESCRIPTION OF THE DRAWINGS

The present invention will now be described, by way of example, with reference to the accompanying drawings in which.

DESCRIPTION OF THE PREFERRED EMBODIMENT

Figure 1:
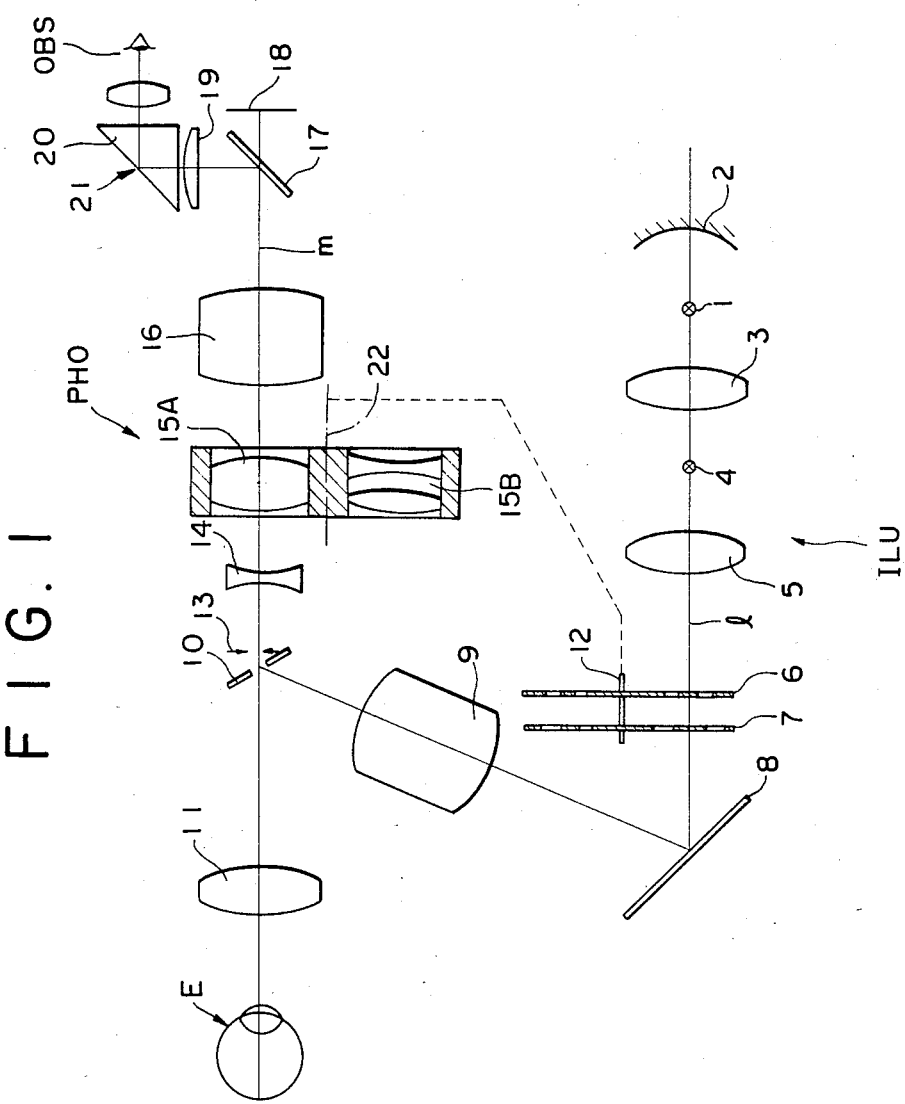
FIG. 1 is a schematic diagram showing the optical systems of an embodiment of the eye fundus camera according to the present invention.

Now referring to FIG. 1, there is shown a schematic diagram of an embodiment of the eye fundus camera according to the present invention. The camera has an illuminating optical system ILU, and a photographing optical system PHO.

The illuminating system ILU includes a first light source 1, which comprises an incandescent-filament lamp, for example, a concave reflecting mirror 2 is provided behind the light source 1. A concave relay lens 3 provided in front of the first light source 1 converges the light emitted from the first light source 1 at a point, where a second light source 4 is provided. The second light source 4 comprises a flash light, for example. The first light source 1 is intended to illuminate the eye fundus for observation, while the second light source 4 for taking a photograph. A relay lens 5 provided in front of the second light source 4 converges the light from the first or second light source toward a pair of parallel rotatable plates 6 and 7, each of which has annular apertures. Details of these plates will be described later.

The light having passed through the apertures of the plates 6 and 7 reaches a reflecting mirror 8, which is inclined at a definite angle with respect to the optical axis 1 of the lenses 3 and 5 and which deflects the light from the plates toward another relay lens 9. A mirror 10 having an opening in the central region threof deflects the light from the lens 9 toward an objective lens 11, through which the light from the illuminating system ILU is projected outwards. The fundus of the eye, directed at a specified distance toward the objective lens 11, is thus illuminated by the light from the illuminating system ILU of the camera.

Figure 2:
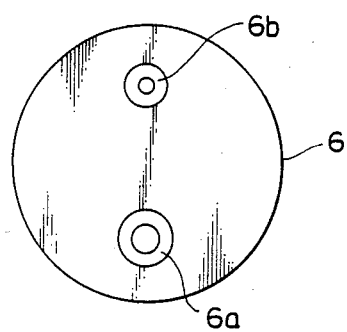
FIGS. 2 and 3 are plan views of a first and second aperture plates respectively.
Figure 3:
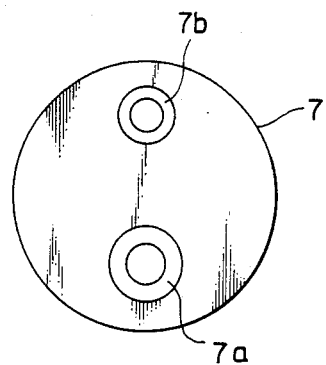

The parallel plates 6 and 7 are rotatable about a common axis 12 which is parallel with the optical axis 1. The position of the first plate 6 is optically conjugate with that of the cornea K of the eye to be inspected (See FIG. 4), while the position of the second plate 7 is optically conjugate with that of the iris R. As shown in FIG. 2, the plate 6 has a pair of annular apertures 6a and 6b, and the inner and outer diameters of one aperture 6a are larger than the inner and outer diameters of the other 6b, respectively. As shown in FIG. 3, the other plate 7 likewise has a pair of annular apertures 7a and 7b, and the inner and outer diameters of one aperture 7a are larger than the inner and outer diameters of the other 7b, respectively. The apertures 6a and 6b of first plate 6 are coaxial with the apertures 7a and 7b of second plate 7, respectively. The combination of larger apertures 6a and 7a and the combination of smaller apertures 6b and 7b are alternately brought into alignment with the optical axis 1 of the lenses 3 and 5 of the illuminating system by rotating the plates 6 and 7 round the axis 12. In this way, the size of the annular images of the apertures to be formed in the eye can be adjusted.

The construction of the photographing system PHO will now be described. The light rays reflected from the eye fundus and entering the objective lens 11 are converged by this lens and then pass through the central opening of the mirror 10 and then reach a diaphragm 13 located at a position near the mirror 10 and optically conjugate with the anterior chamber Z of the eye (see FIG. 4). The light having passed through the diaphragm 13 is diverged by a focusing lens 14 which is displaceable along an optical axis m of the photographing system PHO. Lenses 15A and 15B provided behind the lens 14 can be selectively brought into alignment with the optical axis m to adjust the angle of view. The lenses 15A and 15B are used to take photographs at a wide and a narrow angle of view, respectively. The light rays having passed through the lens 15A or 15B are converged by a convex lens 16 to form an image of the eye fundus on a sensitized film 18.

A movable mirror 17 can be inserted between the lens 16 and the plane of film 18 at a definite angle with respect to the optical axis m to deflect the light from the lens 16 toward a plane 19 which is optically conjugate with the film plane 18. The image of the eye fundus formed on the plane 19 can be observed by an observer OBS through an optical system 21 including a prism 20.

In this embodiment, the focusing lens 14 is moved, or adjusted, along the axis m so as to form the image of the eye fundus in the front focal plane of the lens 15A or 15B, thereby to form the image of the eye fundus on the film plane 18 or the plane 19 for observation. If the image magnification is varied by alternating the lenses 15A and 15B, the image of the eye fundus can be formed on the plane 18 or 19 by adjusting the lens 14.

In this embodiment, the image magnification can be changed over between two values by means of the lenses 15A and 15B. However, it is also possible to have three or more values of image magnification by having as many suitable alternative lenses between the lenses 14 and 16.

It is possible to mount the lenses 15A and 15B on a plate rotatable about an axis 22 parallel with the axis m. In such a case, the plate mounted with the lenses 15A and 15B and the aperture plates 6 and 7 can be interlocked with one another by mechanical means such as chains so as to connect the image magnification adjusting operation with the operation of adjusting the size of the annular apertures, as indicated by broken lines in FIG. 1. Then, the larger apertures 6a and 7a and the lens 15A are inserted into the light path for taking a photograph at a wide angle of view, while the smaller apertures 6b and 7b and the lens 15B for taking a photograph at a narrow angle of view.

Figure 4:
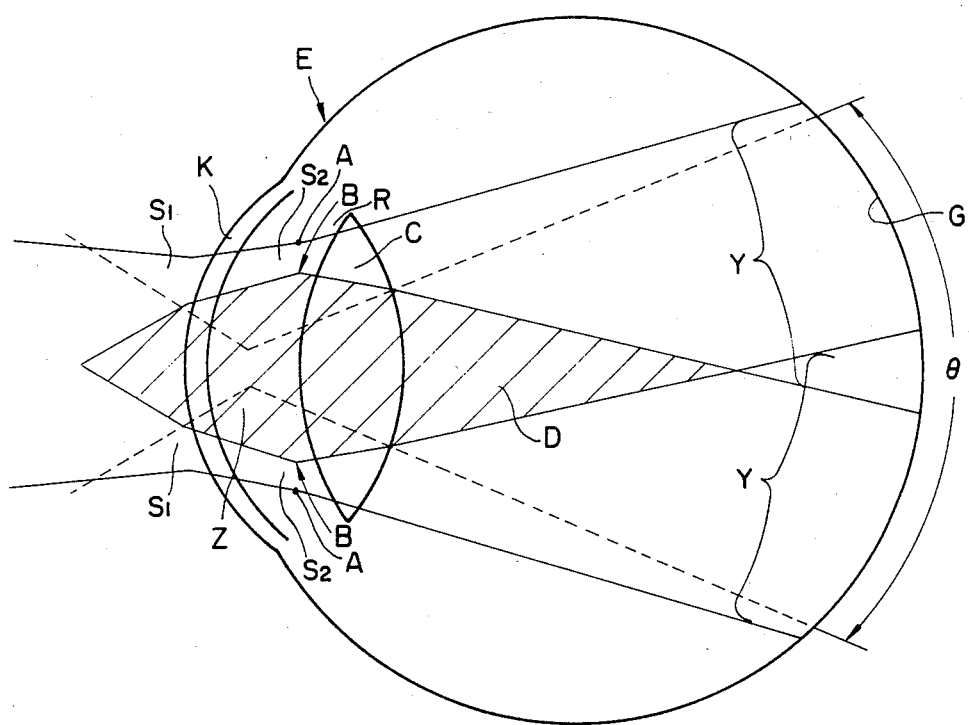
FIG. 4 is a schematic cross sectional view of an eye, showing various bundles of rays of light upon taking a photograph at a wide angle of view.

FIG. 4 shows schematically the path of light in an eye at the time when a photograph is taken at a wide angle of view $\theta$ of e.g. 45°. The bundle of rays of light from the illuminating system ILU is shown by reference Y, and hereinafter called "illuminating light ray bundle". On the other hand, light reflected or scattered from the eye fundus G in directions within the angle $\theta$ can reach the film plane 18, and this bundle is hereinafter called "image forming light ray bundle".

To take a wide angle photograph, the larger annular apertures 6a and 7a are inserted into the path of light. The images S1 and S2 of the apertures 6a and 7a are formed in planes passing through the cornea K and the iris R of the eye respectively, and the eye fundus is illuminated by the illuminating light rays within the bundles Y, as shown in FIG. 4.

There is an area D ("dark area") which is not traversed by the illuminating light rays and in FIG. 4 represented by a symmetrical hexagon filled in with parallel slant lines.

The position of the diaphragm 13 is optically conjugate with a position in the anterior chamber Z of the eye. The inner diameters of the images S1 and S2 of the annular apertures are determined such that the dark area D includes an area traversed by the image forming light rays at the cornea K and the crystalline lens C. As a result, light reflected or scattered from the cornea K or the crystalline lens C will not mingle with the image forming light ray bundle, so that a clear photograph of the eye fundus can be taken without flare or ghost images.

The above mentioned arrangement, in which annular aperture images S1 and S2 are formed in planes passing through the cornea K and the crystalline lens C respectively, is advantageous in that illuminating light rays can be effectively utilized and that the dark area D can be made large. Thus, the larger the angle of view is set, the more advantageous is the arrangement.

The area traversed by the image forming light rays is wider when a wide angle photograph is taken than when a narrow angle photograph is taken. Thus the inner diameters of the annular aperture images S1 and S2 must be set large. However, if the pupil of the eye E is not sufficiently opened and the inner periphery of the iris R is at a position as indicated by reference B in FIG. 4 when the inner diameters of the images S1 and S2 are set large, the illuminating light rays are interrupted by the iris so that the eye fundus is not illuminated and no photograph can be taken. With the camera according to the present invention, photographs can be taken at a narrow angle of view if the pupil is reduced.

Figure 5:
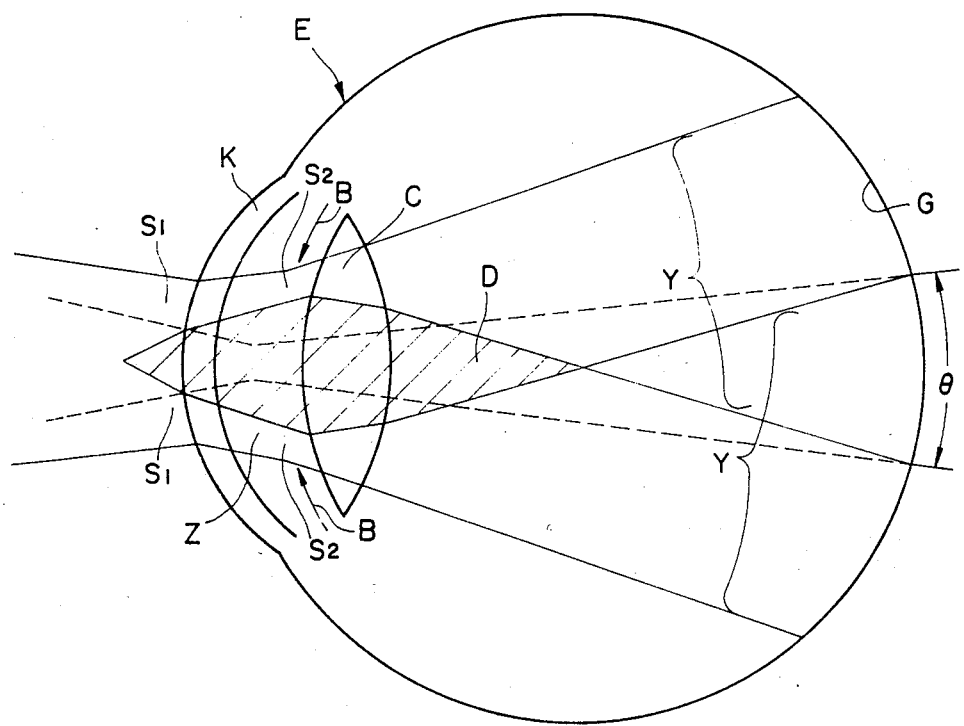
FIG. 5 is a schematic cross sectional view of an eye, showing various bundles of rays of light upon taking a photograph at a narrow angle of view.

FIG. 5 shows the path of rays of light in the eye when a narrow angle photograph is taken. The pupil is not sufficiently opened and the periphery of the iris R is at the position B, as in the case of FIG. 4. The smaller annular apertures 6b and 7b are inserted into the path of light in the illuminating system ILU by rotating the plates 6 and 7 so as to reduce the inner and outer diameters of the images S1 and S2. Then, the illuminating light rays are admitted to the eye fundus without being interrupted by the reduced pupil, and thus a photograph of the eye fundus can be taken.

As seen from FIGS. 4 and 5, the area traversed by the image forming light rays is narrower when a photograph is taken at a narow angle of view than when at a wide angle of view. Therefore, even if the inner diameters of the images S1 and S2 are set smaller than the values for taking wide angle photographs, the dark area D completely includes the area traversed by the image forming light rays, so that a clear photograph of the eye fundus can be taken without being affected by detrimental reflection or scattering of light at the cornea or the crystalline lens.

In the embodiment shown and above described, both aperture images S1 and S2 are adjustable. However, another arrangement in which the aperture image S2 at the iris R alone is adjustable is possible. In the latter arrangement, where the remaining aperture image S1 is maintained constant, the dark area D behind the crystalline lens C is somewhat narrower as compared with the former arrangement, particularly when the image S2 is adjusted to its smaller size. Thus, the latter arrangement is more likely to undergo the influence of the detrimental reflection or scattering of light at the cornea or the crystalline lens; the detrimental reflection or scattering can be more effectively avoided by the simultaneous adjustment of both aperture images.

With another arrangement, in which the inner diameter of the aperture image S1 formed at the cornea K is adjustable but the outer diameter of same is maintained constant, similar advantages can be obtained. However, more uniform illumination of the eye fundus can be obtained where both the inner and outer diameters of the aperture image S1 are adjustable.

In the embodiment shown and described above, the size of the annular aperture images are adjusted by inserting apertures of different size into the light path in the illuminating system. It is also possible to adjust the size of the aperture images by changing the magnifying power of the illuminating system.

As understood from the above description, the variable image-magnification eye fundus camera according to the present invention has an illuminating system which is arranged such that the path of rays of light projected therefrom can be adjusted to vary the size of the annular aperture images. Thus, with the camera according to the present invention, even if the pupil of the eye to be inspected cannot be opened wide enough to take a photograph at a wide angle of view, it is still possible to take a clear photograph at a narrow angle of view without being affected by the detrimental reflection or scattering of light at the cornea or the crystalline lens in the eye. The camera can be used for not only average persons but also particular cases who cannot sufficiently open the pupil of the eye.

What is claimed is:

1. An eye fundus camera comprising:
a first optical system for illuminating the fundus of the eye to be inspected, including at least one light source, and an annular aperture which is provided at a position optically conjugate with the iris of the eye and through which the light emitted from said light source is directed toward the eye so that an image of said annular aperture is formed at or near the iris;
a second optical system for making a photograph of the eye fundus illuminated by said first optical system, including a variable magnification lens system for varying the image magnification; and
means for adjusting the size of said image of said annular aperture, including means for adjusting the inner diameter of said image for providing a smaller image inner diameter when the magnification of the variable magnification lens system is increased.

2. An eye fundus camera as claimed in claim 1, in which said image size adjusting means includes further means for adjusting the outer diameter of said image of said annular aperture.

3. An eye fundus camera as claimed in claim 1, in which said image size adjusting means comprises a plate having therein a plurality of annular apertures with inner diameters different from one another, said apertures being selectively brought into the path of light from said light source.

4. An eye fundus camera as claimed in claim 3, in which means for interlocking said plate and said variable magnification lens system is provided.

5. An eye fundus camera comprising:
a first optical system for illuminating the fundus of the eye to be inspected, including a first annular aperture provided at a first position optically conjugate with the cornea of the eye, a second annular aperture provided at a second position optically conjugate with the iris of the eye, and at least one light source for directing light through said first and second annular apertures toward the eye so that images of said first and second annular apertures are formed at the cornea and iris respectively;
a second optical system for making a photograph of the eye fundus, including a diaphragm, and a variable magnification lens system for varying the image magnification; and
means for adjusting the size of at least one of said images of said annular apertures, including first means for adjusting the inner and outer diameters of said image of said second annular aperture for providing a smaller image inner diameter when the magnification of the variable magnification lens system is increased.

6. An eye fundus camera as claimed in claim 5, in which said image size adjusting means further includes second means for adjusting the inner and outer diameters of said image of said first annular aperture.

7. An eye fundus camera as claimed in claim 6, in which said image size adjusting means further includes means for interlocking said first and second means.

* * * * *